United States Patent
Zhang et al.

(10) Patent No.: US 6,368,877 B1
(45) Date of Patent: Apr. 9, 2002

(54) SELF-ASSEMBLING PEPTIDE SURFACES FOR CELL PATTERNING AND INTERACTIONS

(75) Inventors: Shuguang Zhang, Lexington; Alexander Rich; Lin Yan, both of Cambridge; George Whitesides, Newton, all of MA (US)

(73) Assignees: Massachusetts Institute of Technology; President and Fellows of Harvard College, both of Cambridge, MA (US)

( * ) Notice: Subject to any disclaimer, the term of this patent is extended or adjusted under 35 U.S.C. 154(b) by 0 days.

(21) Appl. No.: 08/882,415

(22) Filed: Jun. 25, 1997

(51) Int. Cl.[7] .................... G01N 33/552; G01N 33/543; C12N 11/14; A61K 38/00

(52) U.S. Cl. .................. 436/527; 426/578; 426/523; 426/524; 426/525; 426/526; 426/528; 426/529; 426/530; 426/531; 435/176; 435/177; 530/326; 530/327; 530/328

(58) Field of Search ................ 436/518, 523–531; 435/176, 177; 530/326, 327, 328

(56) References Cited

U.S. PATENT DOCUMENTS

| | | | |
|---|---|---|---|
| 5,330,911 A | | 7/1994 | Hubbell et al. ........ 435/240.243 |
| 5,512,131 A | * | 4/1996 | Kumar et al. ............ 156/665.1 |
| 5,541,070 A | * | 7/1996 | Kauvar ....................... 435/7.9 |
| 5,620,850 A | | 4/1997 | Bamdad et al. ............. 530/300 |

FOREIGN PATENT DOCUMENTS

| | | |
|---|---|---|
| WO | 96/29629 | 9/1996 |
| WO | 97/07429 | 2/1997 |

OTHER PUBLICATIONS

Zhang et al. Biological Surface Engineering: A Simple System for Cell Pattern Formation, Biomaterials vol. 20, pp. 1213–1220, 1999.*
Lea et al. Manipulation of Proteins on Mica by Atomic Force Microscopy. Langmuir vol. 8, pp. 68–73, Jan. 1992.*
Chaikof et al. Self–Assembling Peptide Monolayers: Endothelial Cell Behavior on Functionalized Metal Substrates. Mat. Res. Soc. Symp. Proc. vol. 414, pp. 17–22, 1996.*
Chemical Abstracts: vol. 125, 1997, abstract No. 257089b, 1997.*
Duschl, C., et al., "Biologically addressable monolayer structures formed by templates of sulfur–bearing molecules," *Biophysical Journal* 67(3) :1229–1237 (Sep. 1994).
Knichel, M. et al., "Utilization of a self–assembled peptide monolayer for an impedimetric immunosensor," *Sensors and Actuators B B28* (2) :85–94 (Aug. 1995).
Keller, T.A., et al., "Reversible oriented immobilization of histidine–tagged proteins on gold surfaces using a chelator thioalkane," *Supramolecular Science* 2:155–160 (1995).
Pale–Grosdemange, C. et al., "Formation of Self–Assembled Monolayers by Chemisorption of Derivatives of Oligo (ethylene glycol) of Structure $HS(CH_2)_{11}(OCH_2CH_2)_mOH$ on Gold," *J. Am. Chem. Soc.*, 113(1) :12–20 (1991).
Prime, K.L. and Whitesides, G.M., "Self–Assembled Organic Monolayers: Model Systems for Studying Adsorption of Proteins at Surfaces," *Science*, 252:1164–1167 (1991).
Prime, K.L. and Whitesides, G.M., "Adsorption of Proteins onto Surfaces Containing End–Attached Oligo (ethylene oxide) : A Model System Using Self–Assembled Monolayers," *J. Am. Chem. Soc.*, 115(23):10714–10721 (1993).
Lopez, G.P., et al., "Fabrication and Imaging of Two–Dimensional Patterns of Proteins Adsorbed on Self–Assembled Monolayers by Scanning Electron Microscopy," *J. Am. Chem. Soc.*, 115(23) :10774–10781 (1993).
Sigal, G.B., et al., "A Self–Assembled Monolayer for the Binding and Study of Histidine–Tagged Proteins by Surface Plasmon Resonance," *Anal. Chem.*, 68:490–497 (1996).
Whitesides, G.M., "Self–Assembling Materials," *Scientific American*, 273:146–149 (1995).
Mrksich, M., et al., "Controlling cell attachment on contoured surfaces with self–assembled monolayers of alkanethiolates on gold," *Proc. Natl. Acad. Sci. USA*, 93:10775–10778 (1996).
You, A.J., et al., "A Miniaturized arrayed assay format for detecting small molecule–protein interactions in cells," *Chem. Biol.*, 4(12) :969–975 (1997).
Lopez et al., "Convenient Methods for Patterning the Adhesion of Mammalian Cells to Surfaces Using Self–Assembled Monolayers of Alkanethiolates on Gold," *J. Am. Chem. Soc.*, 115(13) :5877–5878 (1993).
Mrksich and Whitesides, "Using Self–Assembled Monolayers to Understand the Interactions of Man–Made Surfaces with Proteins and Cells," *Annu. Rev. Biophys. Biomol. Struct.*, 25:55–78 (1996).
Xia, et al., "Microcontact Printing of Octadecylsiloxane on the Surface of Silicon Dioxide and Its Application in Microfabrication," *J. Am. Chem. Soc.* 117:9576–9577 (1995).
Deng, L. et al., "Self–Assembled Monolayers of Alkanethiolates Presenting Tri(propylene sulfoxide) Groups Resist the Adsorption of Protein," *J. Am. Chem. Soc.*, 118(21):5136–5137 (1996).
Chen, C.S. et al., "Geometric Control of Cell Life and Death," *Science*, 276: 1425–1428 (1997).

(List continued on next page.)

Primary Examiner—Jyothsna Venkat
Assistant Examiner—Maurie E. Garcia
(74) Attorney, Agent, or Firm—Hamilton, Brook, Smith & Reynolds, P.C.

(57) ABSTRACT

This invention describes self assembled monolayers (SAMs) manufactured by imprinting reactive peptides onto solid supports. The invention further relates to methods of preparing and using these improved SAMs.

7 Claims, 3 Drawing Sheets

OTHER PUBLICATIONS

Kumar, A. et al., "Patterned Self–assembled Monolayers and Meso–Scale Phenomena," *Acc. Chem. Res.*, 28(5) :219–226 (1995).

DiMilla, P.A. et al., "Wetting and Protein Adsorption of Self–Assembled Monolayers of Alkanethiolates Supported on Transparent Films of Gold," *J. Am. Chem. Soc.*, 116(5) :2225–2226 (1994).

Singhvi, R. et al., "Engineering Cell Shape and Function," *Science*, 264:696–698 (1994).

Wilbur, J.L., et al., "Microfabrication by Microcontact Printing of Self–Assembled Monolayers," *Adv. Mater.*, 6(7/8) :600–604 (1994).

Xia, Y., et al., "Microcontact Printing of Alkanethiols on Copper and Its Application in Microfabrication," *Chem. Mater.*, 8(3) :601–603 (1996).

Mrksich, M., et al., "Biospecific Adsorption of Carbonic Anhydrase to Self–Assembled Monolayers of Alkanethiolates that Present Benzenesulfonamide Groups on Gold," *J. Am. Chem. Soc.*, 117(48) : 12009–12010 (1995).

Jeon, N.L., et al., "Patterned Self–Assembled Monolayers Formed by Microcontact Printing Direct Selective Metalization by Chemical Vapor Deposition on Planar and Nonplanar Substrates," *Langmuir*, 11(8) :3024–3026 (1995).

* cited by examiner

SELF-ASSEMBLING PEPTIDE SURFACES FOR CELL PATTERNING AND INTERACTIONS

GOVERNMENT GRANT

This invention was made with government support under Grant number DAAH04-94-G-0407 awarded by the Department of the Army, Grant number GM30367 awarded by the National Institutes of Health, and Grant number N00014-95-1-1182 awarded by the Navy. The government has certain rights in the invention.

BACKGROUND OF THE INVENTION

Organic surfaces have been employed in numerous methods and systems, including as substrates for ELISA, cell and tissue culture. Self-assembled monolayers (SAMS) are a class of organic surfaces manufactured by imprinting a monolayer of organic compounds with reactive moieties onto a solid support under conditions wherein the compounds react with and bind to the solid support in a single ordered and patterned layer. See, Lopez, et al., "Convenient Methods for Patterning the Adhesion of Mammalian Cells to Surfaces Using Self-Assembled Monolayers of Alkanethiolates on Gold," *J. Am. Chem. Soc.*, 115(13):5877–5878 (1993) and Mrksich and Whitesides, "Using Self-Assembled Monolayers to Understand the Interactions of Man-Made Surfaces with Proteins and Cells", *Annu. Rev. Biophys. Biomol. Struct.*, 25:55–78 (1996). Molecular self-assembly is the spontaneous association of molecules under equilibrium conditions into stable, structurally well-defined order joined by non-covalent bonds. SAMs manufactured to date have linked chemical moieties to solid surfaces through long chain alkyl linkages. Examples of organic compounds which have been patterned on a solid support include alkanethiolates and alkylsiloxanes. The SAMs are manufactured employing a process termed "microcontact printing."

It has been suggested that SAMs can be used to pattern cells on a surface by presenting chemical moieties which bind to the cells on the solid surface. Mrksich and Whitesides, above. However, these molecules, and the resulting SAMs, can be difficult and/or expensive to manufacture. Thus, improvements and cost reductions in the manufacture of SAMs are desirable and are necessary.

SUMMARY OF THE INVENTION

This invention is based upon the discovery that improved SAMs can be manufactured by imprinting reactive self assembling peptides onto solid supports. The SAMs are characterized by ease of manufacture and purification. They are versatile in their ability to readily provide a large variety of chemical reactive moieties, or "presenting groups", to selected targets. For example, the SAM's of the present invention can be readily designed to present ligands to cellular receptors, cell adhesion motifs, antibodies or antigen-binding fragments thereof to cell surface proteins. This preferred class of SAMs can be used to bind a target, e.g. a selected cell or cells, to a predetermined locus on the solid support.

Thus, the invention relates to a composition of matter comprising a solid support and a self-assembled monolayer of linear peptides wherein said peptides bound directly to said solid support through a terminal amino acid in a predetermined pattern. Preferably, the peptides comprise a terminal reactive group, a central linker and a presenting group. The invention also relates to the uses and applications of the SAMs described herein, as will be described in more detail below.

The invention further relates to a method for manufacturing a SAM, or a composition of matter comprising a solid support and a self-assembled monolayer of linear peptides wherein said peptides bound directly to said solid support through a terminal amino acid in a predetermined pattern, comprising microcontact printing the reactive peptides onto the solid support and maintaining the peptides under conditions suitable for binding.

The foregoing and other objects, features and advantages of the invention will be apparent from the following more particular description of preferred embodiments of the invention, as illustrated in the accompanying drawings. The drawings are not necessarily to scale, emphasis instead being placed upon illustrating the principals of the invention.

DETAILED DESCRIPTION OF THE INVENTION

Figure 1:
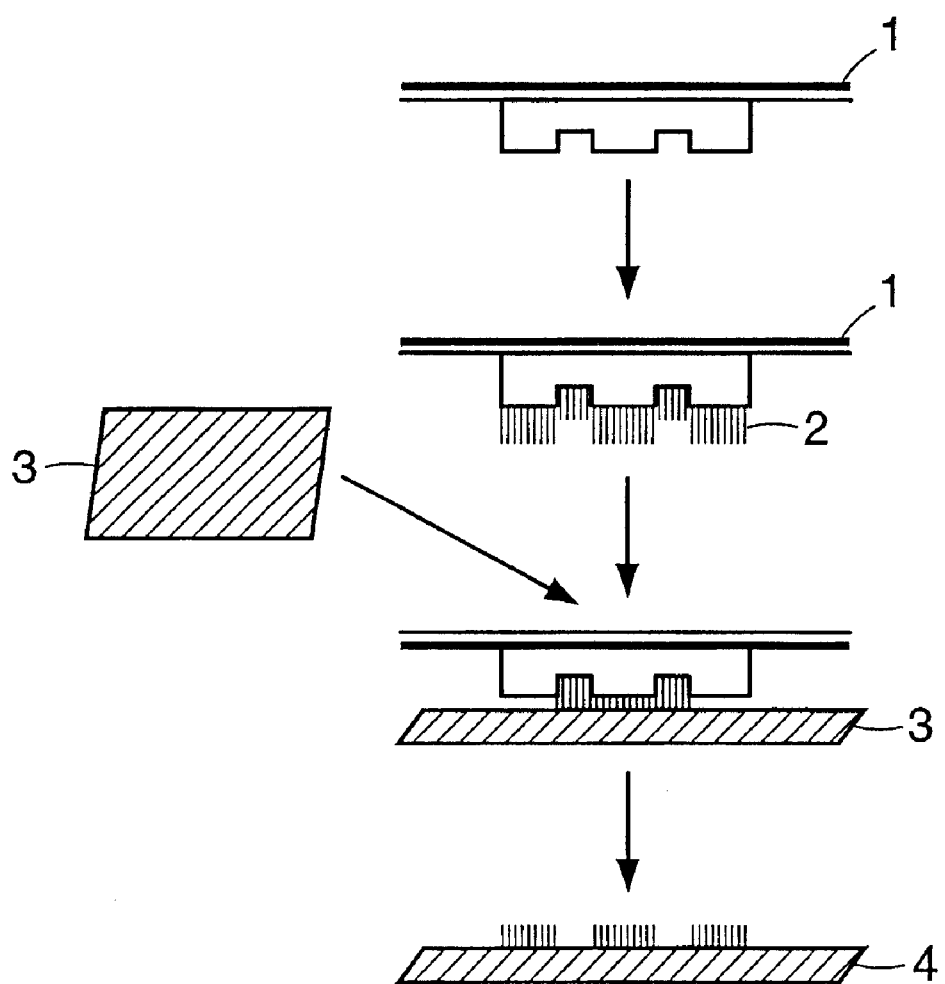
FIGS. 1 and 2 illustrate methods of microcontact printing reactive peptides to a solid support in a predetermined pattern.

As set forth above, the invention relates to improved SAMs comprising a predetermined pattern of peptides on a solid support. Preferred peptides of the invention can be characterized by three regions bound to each other through an amino acid or via peptide binding, the "terminal reactive group", the "central linker" and the "presenting group."

Upon binding the peptides to the solid support, the peptides are preferably highly ordered and preferably possess a consistent linear and parallel configuration with each other. Generally, the peptides, or the central linker thereof, are fully extended beta strands in configuration under the conditions of use.

Although in some embodiments, it may be desirable to present a ligand or other molecule which possesses a tertiary structure, generally, the peptides are linear (e.g., free or substantially free of branching or tertiary structure). "Substantially free" of branching or tertiary structure is intended to include minor amounts of branching and peptide interactions which do not significantly interfere with the free movement or function of the presenting group. The actual degree of branching and peptide interactions which can be tolerated without deleteriously effecting the quality of the product will be a function of the overall length of the peptide, the branched peptides, the nature of the amino acids in each and their ability or tendency to interact with each other can generally be determined by routine screening or computer modeling. For example, peptides "substantially free" of branching may include a peptide composition wherein less than about 5% of the peptides are characterized by one or more branches.

While the length of the peptide is not critical to the invention, the peptide is preferably small to moderate in length. Thus, the central linker of the peptide can preferably be between about 2 to about 50 naturally occurring or non-naturally occurring amino acids in length, more preferably between about 8 to about 35 amino acids in length. Certain peptides in excess of 50 may present undesirable interactions of the peptides, such as a possible tendency of the peptide to fold. Peptide interactions can be predicted by, for example, computer modeling and structural information available at protein data banks at, for example, Brookhaven National Laboratories, N.Y.

Peptides which can be used in the invention can be characterized by a reactive moiety which can react and bind to the solid support, the "terminal reactive group". Typically, the terminal reactive group is an amino acid characterized by a functional group pendant from the side chain, the amino group or the carboxy group. Thus, the terminal reactive group which binds to the solid support can be an amino acid substituted by a hydroxy, thiol, carboxy, amino, amido, imido or guanidino group. Preferred terminal amino acids, thus, include serine, cysteine, tyrosine, asparagine, glutamine, aspartic acid, glutamic acid, lysine, arginine and histidine. Alternatively, the terminal reactive group can be a nonnaturally-occurring amino acid characterized by a functionality which can react with the solid support. Examples include beta amino acids (amino acids wherein the amino and/or carboxy group are not substituted on the same alpha carbon, such as beta-alanine) or amino acids which have been chemically modified, by electrophilic substitution, nucleophilic substitution, activation reactions or addition reactions, for example. See March, "Advanced Organic Chemistry," Third Edition (1985), Chapters 10–16.

It is further desirable that the peptide be of sufficient length to provide a flexible, spatial separation between the solid support (upon reaction with the reactive terminal group) and the opposing reactive terminus of the peptide (e.g., the presenting group). Thus, the peptides of the invention preferably comprise a "central linker", which is a peptide bound to the terminal reactive group and presenting group through peptide or amide bonds. The amino acids employed in the peptide and/or central linker are selected to promote or optimize a beta strand configuration at the conditions for use. It is further preferred that the amino acids in this portion of the peptide be substantially free of large or bulky side chains or bonds which will interfere with the configuration (e.g. proline). The amino acids can further be selected considering material strength, permeability and degradation rate of the resulting peptide and SAM. Preferably, the amino acids selected for the central section of the peptide are glycine, L-alanine and D-alanine. D-amino acids have advantages in many applications due to their resistance to L-protease degradation.

The length of the central linker where present, is also generally not critical to the invention. Preferably, the central linker is between about 2 and about 30 amino acids in length, more preferably between about 2 and about 8 amino acids.

The peptide can also be characterized by a "presenting moiety" which will bind to one or more targets. The term "presenting group" is defined herein to include one or more chemical atoms, functional groups, amino acids or peptides that possess an affinity to or resistance for a target entity. For example, a presenting group which presents a resistance for a target entity, e.g., a protein or cell, can be poly(ethylene glycol) or another compound which is inert to the target. A presenting group which is resistant to water, as a target molecule, is a hydrophobic group, such as a high chain alkyl or hydrophobically blocked amino acid (e.g., an alkyl ester of valine, leucine, isoleucine or phenylalanine).

Generally, one or more peptides employed in the present invention possess a presenting group with an affinity for a target, e.g. a target molecule. In such embodiments, the presenting group can be specific or non-specific for the target molecule. For example, where the target is a cell, the target molecule can be a cell surface protein. The presenting group can be a ligand for that protein, an antibody or an antigen-binding fragment thereof which binds specifically to the cell surface protein.

The presenting group can be a non-peptide or, preferably, a peptide. As discussed above, the presenting group can be a ligand for or an antibody or antibody fragment which binds to the target molecule.

Particularly suitable presenting groups are oligopeptides which self assemble to form a beta sheet under conditions for the desired or selected application. Examples of oligopeptides which self assemble under these conditions are described in U.S. Pat. No. 5,670,483 and U.S. application Ser. No. 08/784,606, which are incorporated herein by reference in their entireties. Briefly, these oligopeptides are amphiphilic, have alternating hydrophobic and hydrophilic amino acids and are self-complementary. As will be described in more detail below, particularly preferred oligopeptides for self assembly are $(RADX)_n$(SEQ ID No:2) and $(EAKX)_n$(SEQ ID No:4) $EAKX_n$ wherein X is an amino acid and n is an integer between about 2 and about 8.

Particularly preferred targets include cells. Examples of cells which can be targeted include prokaryotic and eukaryotic cells. The cells can be mammalian, plant, bacterial, and yeast. Mammalian cells which can be targeted include tumor cells, normal somatic cells and stem cells. The cells can be fibroblasts, endothelial cells, neuronal cells, hepatocytes, blood cells, smooth muscle cells, and progenitors thereof, for example. Bacterial cells can be gram positive or gram negative bacteria and can include *Escherichia coli, Streptococcus, Staphylococcus,* as well as many others. Bacterial cells which may be desirable to target and, thus detect and/or culture, can include pathogens and non-pathogens, e.g., contaminants in a food sample, a mammalian tissue sample or serum sample or in a plant tissue sample. Similarly, yeast can be targeted and include, for example, Candida and Saccharomyces.

Cells can preferably be targeted by selecting a presenting group which will react with and bind to the cell surface. Generally, this is accomplished by binding to a cell surface molecule, such as a protein, lipid, or sugar at the surface of the protein. These surface molecules are included herein as "target molecules." For example, a target molecule can be a cell surface protein and can be specific to the target or, in this case, cell, or the target molecule can be non-specific. Where the object of the application is to detect the presence of a cell in a sample, e.g., a tumor cell in a sample which can contain normal cells, it is desirable that the target molecule be specific to the tumor cell (e.g., present on tumor cells and absent on the normal cells). These molecules are generally known in the art as tumor markers. Where the object of the invention is to detect the presence of bacteria in a sample, such as in food, tissue sample, blood sample, or pharmaceutical, it can be desirable to select a target molecule which is present on many types of bacteria which are potentially contaminating the sample to be tested. In other instances, e.g., where a substantially pure cell culture is being targeted or transferred to the solid support, the selection of specific or non-specific target molecule is immaterial.

Suitable target molecules include tumor markers, cellular receptors, such as CD4 and,CD8. Neuronal cellular receptors include N-CAMs, the L1 receptors, NGF receptor, the netrin receptor and others.

Targets can include non-cellular products as well, including viruses (such as retroviruses, influenza viruses, and herpesviruses, for example), and proteins (such as prostate soluble antigen (PSA), cytokines, cytokine receptors, growth factors, and growth factor receptors. Where the target is a virus, the target molecule can be a surface protein as well, such as a cellular receptor implicated in the infection of cells. A particularly preferred target molecule for HIV is, for example, gp120.

Examples of presenting groups include cellular adhesion motifs, ligands or binding fragments of ligands for the target molecule (e.g., the ligand for gp120 is CD4), antibodies or antigen binding fragments of antibodies which bind to the target molecule.

A ligand is defined here to include molecules which are the same as or substantially the same as the native molecule which binds the target molecule. For example, CD4 is a native ligand for the HIV env protein, gp120. Thus, where the target molecule is gp120, the term "ligand" and, thus, the presenting groups include native CD4, a ligand-binding fragment of CD4 (such as, an extracellular domain), and mutations thereof which bind to gp120.

The terminal reactive group, central linker and presenting group are preferably arranged linearly with the central linker bonded directly or indirectly to both the reactive group and the presenting group through, e.g., peptide bonds. Preferably, the peptide has the formula:

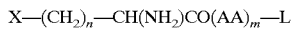

or

wherein

X is an inert group, such as H, alkyl, alkoxy, alkylthio or dialkylamine, or is a labile or reactive group, such as a thiol, hydroxy, amino, carboxy, acylhalide, carboxy ester, or halide;

AA is, independently, the same or different, naturally-occurring or non-naturally-occurring amino acid, and is preferably, glycine, L-alanine or D-alanine;

L is a group which binds specifically or non-specifically to a target and is preferably a peptide, such as a ligand, an antibody or an antibody fragment;

n is zero or an integer between 1 to about 5;

m is an integer of at least about 2 and, preferably, between about 2 and about 50, more preferably between about 2 and about 8.

The peptides of the invention can be manufactured by known and industry standard peptide synthesis technology. For example, the peptides can be synthesized chemically or recombinantly (e.g. by the expression of a recombinant nucleic acid molecule which encodes the peptide or a precursor thereof). A precursor of the peptide can be particularly beneficial where one or more of the amino acids are non-naturally occurring (e.g. a beta amino acid or an amino acid with a non-naturally occurring side chain). The manufacture of peptides chemically and recombinantly are generally practiced in the art and are described in, for example, United States application Ser. Nos.: 08/346,849 and 08/784,606 and Ausubel, *Current Protocols in Molecular Biology* (1997). The peptides can preferably be purified prior to use in the manufacture of the SAMs by standard techniques, including HPLC.

The peptides employed in the invention are imprinted or patterned on a solid support. The shape of the solid support is not critical to the invention and can be selected to optimize ease of use in the particular application. Thus, the solid support can be substantially spherical (e.g., a bead) or non-spherical, such as in a container (e.g., a petri dish or cup), cylinder or cone, or a substantially flat film, stick, chip or disc, of essentially any size suitable for the ultimate application. The solid support can be porous (as in a membrane) or non-porous (as in a petri dish or container).

The material employed in the manufacture of the solid support is not critical as well. Thus, a variety of materials can be employed in the manufacture of the solid support. For example, the solid support can be an inorganic material such as a metal, including as gold, copper, zinc, silver or nickel or a metal alloy. Alternatively, the solid support can be glass, silica, or silicon oxide. In yet another embodiment, the solid support can be an organic material, such as a polymer or resin, including nylon, poly(ethylene glycol), and polyfluoropolymers. It can be desirable in some embodiments to employ a transparent solid support. In this embodiment, the detection of the binding of an opaque target (e.g., a cell) can be determined readily and accurately visually or electronically and/or robotically employing, for example, a laser under the control of a computer.

The solid support is selected with a view towards its ability to react with the terminal reactive group of the peptide. For example, the thiol group (e.g., X) can react with gold under standard methods, as described, for example in Mrkisch and Whitesides, above. Likewise, the hydroxy group (e.g., X) can react with siloxane under relatively mild conditions. Xia, et al. "Microcontact Printing of Octadecylsiloxane on the Surface of Silicon Dioxide and Its Application in Microfabrication," *J. Am. Chem. Soc.* 117:9576–9577 (1995).

Solid supports which are inert to the peptide can be derivatized to render them reactive. For example, the solid support can be coated with a reactive material, chemically treated (e.g., by electrophilic or nucleophilic substitution reaction, addition reactions, etc.) to introduce reactive groups.

The peptides are printed on the solid support, as will be described below. The terms "printed", "patterned" or "predetermined pattern" are defined herein to mean that the solid support has ordered areas where the peptides are bonded and not bonded to the solid support. That is, a printed or patterned solid support is expressly not intended to include a support with random or substantially homogeneous distribution of the peptide over its entire surface(s). Furthermore, the peptides are printed on the solid support in a single layer in a substantially consistent configuration. Thus, the terms are further not intended to include solid supports wherein peptides are bonded to the solid support via distinct and different functional groups across the same molecule (e.g., distinct cysteine residues in a protein containing multiple cysteines along its sequence).

Figure 3:
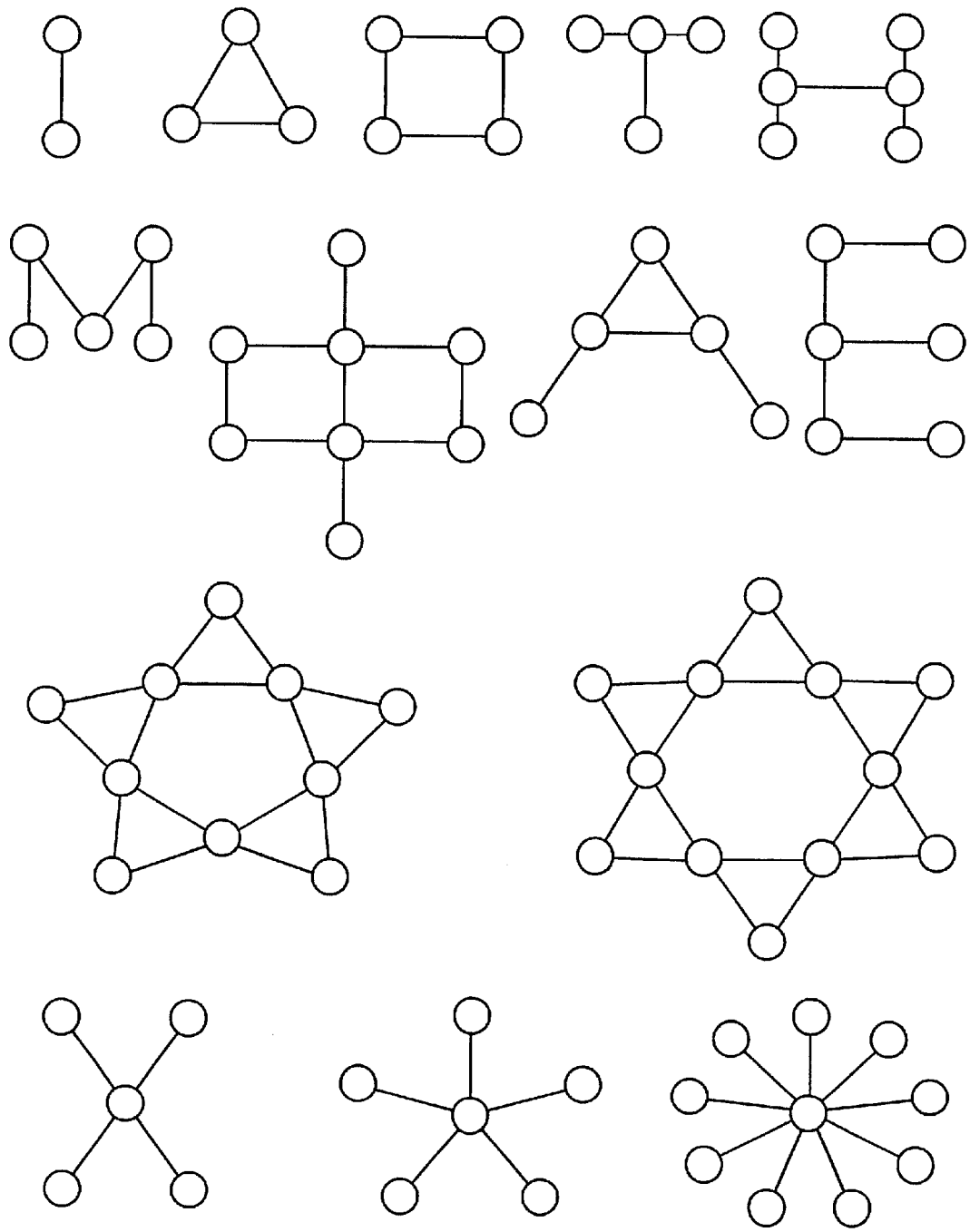
FIG. 3 illustrates patterns which may be selected, for example, in SAMs for immobilizing cells.

The patterns which can be selected in this invention are not particularly critical. Preferred patterns for SAMs useful as research tools in the study of cell/cell interactions are linear tracks of alternating peptides which can adhere to the cells and inert tracks of solid support or an inert compound bound to the solid support. Depending upon the thickness of the tracks, the orientation of the cell can further be manipulated. That is a thin track can result in the orientation of the cells linearly. FIG. 3 exemplifies suitable patterns.

As stated above, methods for the manufacture of SAMs are generally known in the art. U.S. Pat. Nos.: 5,620,850 and 5,512,131 the contents of which are incorporated herein by reference and PCT Published Application Nos.: WO97/07429 and WO96/29629 decribed suitable methods for manufacture. Additional examples include Deng,-Li, Milan Mrksich and George M. Whitesides, "Self-Assembled Monolayers of Alkanethiolates Presenting Tri(propylene sulfoxide) Groups Resist the Adsorption of Protein," *J. Am.*

*Chem. Soc.,* 118(21):5136–5137 (1996); Chen, Christopher S., Milan Mrksich, Sui Huang, George M. Whitesides, Donald E. Ingber, "Geometric Control of Cell Life and Death," *Science,* 276:1425–1428 (1997); López, Gabriel P., Mark W. Albers, Stuart L. Schreiber, Reed Carroll, Ernest Peralta, and George M. Whitesides, "Convenient Methods for Patterning the Adhesion of Mammalian Cells to Surfaces Using Self-Assembled Monolayers of Alkanethiolates on Gold," *J. Am. Chem. Soc.,* 115(13):5877–5878 (1993); Kumar, Amit, Nicholas L. Abbott, Enoch Kim, Hans A. Biebuyck, and George M. Whitesides, "Patterned Self-Assembled Monolayers and Meso-Scale Phenomena," *Acc. Chem. Res.,* 28(5):219–226 (1995); DiMilla, Paul A., John P. Folkers, Hans A. Biebuyck, Ralph Härter, Gabriel P. López, and George M. Whitesides, "Wetting and Protein Adsorption of Self-Assembled Monolayers of Alkanethiolates Supported on Transparent Films of Gold," *J. Am. Chem. Soc.,* 116(5):2225–2226 (1994); Singhvi, Rahul, Amit Kumar, Gabriel P. Lopez, Gregory N. Stephanopoulos, Daniel I. C. Wang, George M. Whitesides, Donald E. Ingber, "Engineering Cell Shape and Function," *Science,* 264:696–698 (1994); Mrksich, Milan and George M. Whitesides, "Using Self-Assembled Monolayers to Understand the Interactions of Man-Made Surfaces with Proteins and Cells," *Annu. Rev. Biophys. Biomol. Struct.,* 25:55–78 (1996); Wilbur, James L., Amit Kumar, Enoch Kim, George M. Whitesides, "Microfabrication by Microcontact Printing of Self-Assembled Monolayers," *Adv. Mater.* 6(7/8):600–604 (1994); Xia, Younan, Enoch Kim, Milan Mrksich and George M. Whitesides, "Microcontact Printing of Alkanethiols on Copper and Its Application in Microfabrication," *Chem. Mater.* 8(3):601–603 (1996); Mrksich, Milan, Jocelyn R. Grunwell and George M. Whitesides, "Biospecific Adsorption of Carbonic Anhydrase to Self-Assembled Monolayers of Alkanethiolates that Present Benzenesulfonamide Groups on Gold," *J. Am. Chem. Soc.,* 117(48) :12009–12010 (1995); Jeon, Noo Li, Ralph G. Nuzzo, Younan Xia, Milan Mrksich, and George M. Whitesides, "Patterned Self-Assembled Monolayers Formed by Microcontact Printing Direct Selective Metalization by Chemical Vapor Deposition on Planar and Nonplanar Substrates," *Langmuir,* 11(8):3024–3026 (1995); Xia, Younan, Milan Mrksich, Enoch Kim and George M. Whitesides, "Microcontact Printing of Octadecylsiloxane on the Surface of Silicon Dioxide and Its Application in Microfabrication," *J. Am. Chem. Soc.,* 117(37):9576–9577 (1995). The method is illustrated in FIGS. 1 and 2.

Figure 2:
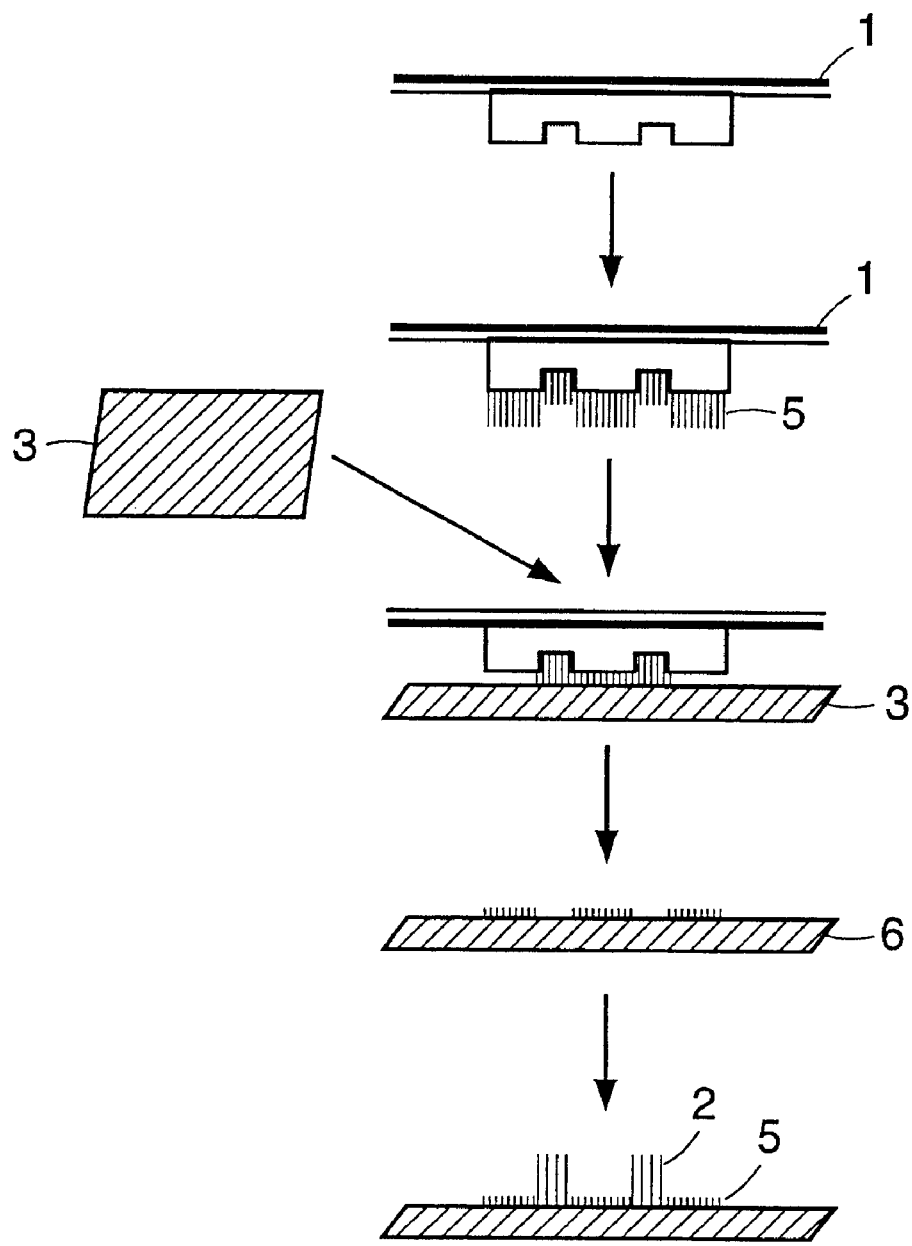

Referring specifically to FIG. 1, a polymeric or elastomeric stamp 1 (e.g. a polydimethylsiloxane stamp) is contacted or "inked" with a solution 2 containing the peptide in a suitable solvent and then the inked stamp is pressed against the solid support 3, thereby transferring the peptide solution in a controlled fashion to the solid support 3. The peptide is then maintained in contact with the solid support 3 under conditions suitable for binding, resulting in a SAM 4.

Upon binding of the peptide to the solid support, the solvent is generally removed, for example, by washing (e.g., extraction), evaporation or lyophilization.

The patterned SAM thus formed can then be used directly or can be further derivatized, e.g., by subjecting the SAM to a second printing step to ink a different chemical compound thereon. The second chemical compound can preferably be a peptide of the claimed invention or can be different, such as an alkanethiol or poly(ethylene glycol), as described in Mrksich and Whitesides, above.

In yet another alternative, the SAM can be subjected to additional steps which can modify the peptide on the SAM. This embodiment may be desirable where the presenting group (e.g., L) or the chemical bond to the central linker ($(AA)_m$) is labile under the conditions for binding the peptide to the solid support. Thus, the presenting group can be chemically reacted with a peptide precursor bonded directly to the solid support, thereby obtaining a SAM of the present invention.

In many instances, it can be desirable to modify the exposed areas of the solid support, for example, by exposing the SAM to ultraviolet light or oxidize the SAM. This can be done to improve the reactivity or eliminate reactivity of the material of the solid support with one or more materials encountered in storage or in use of the SAM.

Referring to FIG. 2, the solid support 3 is stamped with a solution containing a first compound 5 (such as a poly (alkoxyglycothiol)) which can react with the solid support and presents an imprint or pattern of the solid support, as described above. The printed solid support 6 is then contacted with a solution containing the peptide 2 under conditions suitable for reacting the peptide with the exposed solid support. The thus formed SAM 7 possess a pattern of the peptide in the relief of the imprint of the first compound. The SAM can then be washed and dried, as above. The printed solid support 6 can be immersed into a solution of the peptide or the peptide can be poured or sprayed onto the surface of the SAM, as is convenient.

Solvents which can be used to ink the peptide onto the stamp and, then, onto the solid support include solvents which can disperse or, preferably, solubilize the peptide. The solvent is preferably readily removed, for example, by evaporation, lyophilization or extraction, from the solid support. Examples of preferred solvents include alcohols, such as ethanol, acetone, acetonitrile, DMSO and DMF and miscible combinations thereof. The peptide solution concentration is selected such that the desired amount of peptide is delivered to the solid support. That is, if it is desired to print the peptide upon the solid support at a high concentration or density, then the peptide solution can be at or near the saturation level of a good solvent. If it is desired to imprint a low concentration of the peptide sparsely upon the solid support, the solution can be characterized by a low concentration such as employing a dilute solution.

The solution comprising the peptide can also include additional components. For example, a dispersant or solubilizer can be added to the solution to solubilize or disperse, for example, the peptide. It can be desirable in some instances to include a colorant in the solution, particularly where the solution is colorless or is difficult to observe on the solid support or stamp, so that the area of the solid support which has been inked can be visually observed. It is generally desirable where additional components are added to the solution that they can be readily removed from, e.g. washed free of, the solid support.

It is clear that, in the method for manufacturing the SAMs, either the stamp, solid support or both can be mobile, relative to the other. That is, the stamp can be fixed and the solid support pressed firmly against it or vice versa. Alternatively, both the stamp and support can be mobilized. This process can be readily achieved employing robotics, which ensures a high degree of consistency and accuracy in the printing step.

The peptide can be bound to the solid support via covalent bonding, ionic bonding or other chemical interactions. It is preferred that the bonding be of a high affinity and be essentially irreversible under the conditions for use. The conditions suitable for bonding the peptide to the solid support can be dependent upon the nature of the chemical reaction relied upon and can generally be determined by the person of skill employing no more than routine skill.

Clearly, other methods for the manufacture of the SAMs of the present invention will be apparent to the person of skill in the art and are intended to be included within the scope of the present invention.

The SAMs of the invention can be employed in a variety of processes in biology, biotechnology, medicine, material science, biomedical engineering and computer-related inventions. A preferred example of an application includes the use of the SAMs as substrates for ELISA.

SAMs to Screen for the Presence of a Target in a Sample

The SAMs of the present invention can be used to screen for the presence of a target in a sample. As set forth above, the SAMs of the invention can be designed to possess a presenting group which binds specifically or non-specifically to a target or target molecule. Where the presence of a cell is to be detected and distinguished from other cells in the sample (e.g.,the presence of a tumor cell in a tissue sample which can further comprise normal diploid cells), the presenting group is "specific" to the target, i.e. does not bind substantially to other materials or cells which can be present. Where the presence of many different cells in a sample (e.g., the presence of bacterial contaminants in a pharmaceutical process stream), the presenting group is non-specific to a particular target but can bind to a large number of targets.

The method of screening for the presence of a target can comprise the steps of contacting an SAM, as described above, with a sample under conditions suitable for the target or target molecule to bind to the presenting group on the SAM and detecting the presence of the target or target molecule. The target or target molecule can be a cell, such as a mammalian cell (e.g.,tumor cell, normal diploid somatic cell, or stem cell), a bacterium or yeast (e.g., a causative agent for disease or contaminant). Alternatively, the target or target molecule can be a virus (e.g., a causative agent for disease or contaminant), toxin or protein, etc.

The sample can be obtained from an animal or patient, such as a tissue sample or biopsy, body fluid, e.g., serum, milk, saliva or urine or fecal matter. Alternatively, the sample can be obtained from manufacturing process, such as a pharmaceutical process or food process. Thus, the method can be used to screen for contaminants or sterile conditions in manufacturing or it can be used to screen for or diagnose disease in a patient.

It is generally desirable that the sample be contacted with the SAM as a liquid, e.g. a dispersion or solution. Thus, the sample can be mixed with a diluent or buffer. Examples of diluents include water, such as sterile water, polar and non-polar solvents, e.g. alcohols, dimethylformamide, acetonitrile, alkanes, benzene, toluene, etc. Buffers include physiological buffers, such as phosphate buffered solution, culture media, etc.

The person of skill in the art can determine empirically the conditions for contacting the SAM and the sample such that the target or target molecule can react with each other and bind. Such conditions are well known in the art. Generally, where the method is a diagnostic tool and the sample is a tissue sample or other biological sample, the conditions will physiologic. That is, physiological pH is generally employed. Room temperature can also be employed in many instances. Where the method is detecting the presence of contaminants in a sample, neutral pH can be generally employed, as well as room temperature.

The SAM can be contacted with the sample in a number of ways. For example, the SAM can be immersed into the sample, as in dipping a stick. Alternatively, the sample can be poured over or through the SAM. Optionally, the SAM can be rinsed after the contacting step, such as with sterile water.

After the SAM has been contacted with the sample, the presence of the target or target molecule is detected. This can also be performed in a number of ways. In one embodiment, the SAM can be contacted with a second solution which possesses a labeled compound which can react with the target molecule, as in an ELISA method. The label (e.g., a calorimetric label or radiolabel) can then be detected. In many embodiments, the target can be detected visually, with the naked eye, under a microscope or robotically. This can be advantageous, for example, where the target is a cell. In many embodiments, it may be desirable to permit any cells bound to the SAM to colonize prior to detection. The method of the invention can accurately determine the presence of an individual cell or determine a precise cell count in a sample.

In a particularly preferred method, the solid support for the SAM is transparent. In such an embodiment, the presence of an opaque target, such as a cell, can be determined by scanning the SAM with a laser and determining the number of targets or cells present thereon, which accurately correlates to the number of interruptions in scanning. This method can be performed in an automated system (e.g. robotically), thereby improving efficiency and avoiding inaccurate results due to human error.

Sams in Cell Culture

The SAMs of the invention can be used as a solid support in culturing cells. Cells can be attached to the SAMs by contacting the cells to be attached with the SAM and maintaining the cells under conditions suitable for growth. As above, it is generally desirable to contact the cells with the SAM as a liquid, e.g., in the presence of a diluent or solvent. The cells can be attached to the solid support in a predetermined fashion, order and orientation.

Conditions for maintaining cells can be those employed routinely for the cell or cell type to be cultures. For example, the culture can be maintained under temperatures (e.g. between about 25° C. to about 60° C.) and pH (e.g. between about 4 and about 10) appropriate for growth. Nutrients appropriate for growth can also advantageously be provided to the culture.

The invention permits very accurate control of cell population and density. The invention can be utilized to study cell growth and cellular interactions to external stimuli, including other cells, growth factors, repellants and inhibitors. Thus, the invention represents a significant advance in the ability to conduct research in biology and medicine.

In yet another embodiment, the method can be employed in screenings or assays employing cells, such as screening for drugs which may inhibit the growth of a cell or cells (such as in a screen for anti-tumor agents, anti-bacterials). Alternatively, the method can be employed in the screening for drugs which increase or activate the growth of a cell or cells, including fibroblasts, endothelial cells, smooth muscle cells, hematopoietic cells and neuronal cells, etc.

The method can also be used to maintain cell cultures, including tissue cultures, in the manufacture of cellular products (e.g., proteins, hormones, etc.), artificial tissues, etc. Examples of tissues which can be cultured in this manner include fibroblasts, endothelial cells, smooth muscle cells and neuronal cells. Such tissues can be employed as grafts, such as autologous grafts.

The understanding of complex neuronal connections is central to our comprehension of central nervous system function, and advances in doing so will benefit from combining engineering with molecular cell biology to analyze neuronal behavior under well-characterized and controlled conditions. Neurite outgrowth, guidance and connections can be studied on surfaces patterned with self-assembling peptides that contain cell-adhesion motifs. Controlling neurite outgrowth, including distances, angles and direction, can be important in controlling and studying synapse formation between neuronal cells guided into proximity. Neuronal cells attached to the described SAMs can be employed in the study of neuronal cell culture, synapse formation, neuronal connection engineering, screening neuropeptides, as well as pharmaceutical agents that stimulate, inhibit or alter the nature of nerve growth, and inter-connections. For example, attractants, e.g., growth factors, neuropeptides, neurotrophins, and drugs can be screened for their ability to alter the direction or growth behavior of neurites or their ability to induce, stimulate, suppress or inhibit neurite growth. These attractants can be placed or randomly contacted with the neuronal cell-bound SAMs.

Preferred peptides for the manufacture of the SAMs for this application include peptides wherein the presenting group is a cell adhesion motif or peptide which binds to neuronal cells. Examples of suitable cell adhesion motifs are (RADX)(SEQ ID No:2), (RADS)$_n$(SEQ ID No:3), (EAKX)$_n$ (SEQ ID No:4), and (EAKS)$_n$(SEQ ID No:5), wherein X is an amino acid, such as S, and n is an integer, preferably between about 2 to about 8. Oligopeptides of these sequences have been shown to promote neurite outgrowth in culture (U.S. application Ser. No. 08/784,606, which is incorporated herein by reference in its entirety).

EXAMPLE 1

Preparation of patterned SAMs glass chip

A polydimethylsiloxane (hereinafter "ODMS") stamp was prepared from a 10:1 (w:w) mixture of SYLGARD Silicone Elastomer 184 and SYLGARD Curing Agent 184 (Dow Corning Corp., Midland, Mich.) was casted over a master, which was generated by photolithography, and pressure degassed. After sitting at room temperature for 1 hour, the PDMS was cured at 60° C. for 2 hours. The stamp was carefully peeled off the master after cooling to room temperature and rinsed with ethanol. The PDMS stamp was inked by a cotton swab which has been moistened with a 5 mM solution of (1-mercaptoundec-11-yl)hexa(ethylene glycol) $(HO(CH_2CH_2O)_6(CH_2)_{11}SH)$ in ethanol. The resulting stamp was placed on the gold substrate (125 Å gold on a titanium-primed 24×50-2 microscope cover glass) and gentle hand pressure was applied to aid in complete contact between the stamp and the glass chip. After 1 minute, the stamp was peeled off the glass chip and the resulting substrate was immersed directly in a 2 mM solution of $(RADC)_3$ AAAC (SEQ ID NO:1) in distilled, deionized water. After approximately 2 hours of immesion, the glass chip was removed from the solution, rinsed extensively with water and ethanol, and dried with a stream of filtered nitrogen gas.

In our preliminary experiments, when the cells (of various types) are plated on surfaces coated with hexaethyleneglycolthiol, (EG)6-SH, they rarely attach to the surface. In contrast, cells attached very well when plated on the surface coated with the "RADSC" peptide. In these experiments, after cell attachment, the plates containing cells were stacked at 150 rpm for 10 minutes and the coated cover-slides were washed in new medium and transferred to new plates in order to eliminate unattached cells.

Equivalents

Those skilled in the art will recognize, or be able to ascertain, using no more than routine experimentation, many equivalents to the specific embodiments of the invention described specifically herein. Such equivalents are intended to be encompassed in the scope of the following claims:

We claim:

1. A method for manufacturing a composition of matter comprising: 1) a solid support; and 2) a printed pattern comprising a self-assembled monolayer of linear peptides, wherein said peptides are bound to said solid support by a bond between the solid support and a terminal amino acid, said method comprising the steps:
    (a) contacting an elastomeric stamp characterized by a relief of said pattern with a solution containing said linear peptide;
    (b) contacting said stamp with a surface of said solid support under conditions suitable for the reaction between said linear peptide and said solid surface, wherein said linear peptide reacts with said solid support at points of contact between said stamp and said solid support, corresponding to the pattern; and
    (c) removing said stamp.

2. A composition of matter comprising: 1) a solid support; and 2) a printed pattern comprising a self-assembled monolayer of two or more different linear peptides, wherein said peptides are bound to said solid support by a bond between the solid support and a terminal amino acid.

3. A composition of matter comprising: 1) a solid support; 2) and a printed pattern comprising a self-assembled monolayer of linear peptides,
    wherein said peptides are bound to said solid support by a bond between the solid support and a terminal amino acid,
    wherein said peptides comprise a terminal reactive group, a central linker and a presenting group selected from the group consisting of antigens, antibodies, antibody fragments, cellular adhesion motifs, high chain alkyls, hydrophobically blocked amino acids and ligands, and
    wherein said peptides are extended beta strands.

4. A composition of matter comprising: 1) a solid support; 2) and a printed pattern comprising a self-assembled monolayer of linear peptides,
    wherein said peptides are bound to said solid support by a bond between the solid support and a terminal amino acid, wherein said peptides comprise a terminal reactive group, a central linker and a presenting group selected from the group consisting of antigens, antibodies, antibody fragments, cellular adhesion motifs, high chain alkyls, hydrophobically blocked amino acids and ligands, wherein said terminal amino acid is selected from the group consisting of scrine, aspartic acid, glutamic acid and cysteine, wherein said central linker comprises between 2 to 50 amino acids, and wherein said central linker is selected from the group conisisting of a oligoglycine and oligoalanine.

5. The composition of matter according to claim 4 wherein said presenting group possesses an affinity to a target molecule.

6. The composition of matter according to claim 5 wherein the target molecule is a cell surface protein and the presenting group is selected from the group consisting of a ligand, an antibody or an antibody fragment which binds specifically to the cell surface protein.

7. A composition of matter comprising: 1) a solid support; and 2) a printed pattern comprising a self-assembled monolayer of two or more different linear peptides, wherein said peptides are bound to said solid support by a bond between the solid support and a terminal amino acid, the peptide further being characterized by the formula:

or

wherein

X is H, alkyl, alkoxy, alkylthio or dialkylamine, thiol, hydroxy, amino or carboxy;

each AA is independently the same or different and is a naturally-occurring or non-naturally-occurring amino acid;

L is a group which binds specifically or non-specifically to a target;

n is zero or an integer between 1 to 5; and m is an integer of at least 2.

* * * * *

UNITED STATES PATENT AND TRADEMARK OFFICE
CERTIFICATE OF CORRECTION

PATENT NO. : 6,368,877 B1
DATED : April 9, 2002
INVENTOR(S) : Shuguang Zhang, Alexander Rich, Lin Yan and George Whitesides Page 1 of 1

It is certified that error appears in the above-identified patent and that said Letters Patent is hereby corrected as shown below:

Column 15,
Line 7, delete "scrine" and insert -- serine --.

Signed and Sealed this

Twenty-eighth Day of May, 2002

Attest:

*Attesting Officer*

JAMES E. ROGAN
*Director of the United States Patent and Trademark Office*

SEQUENCE LISTING

```
<160> NUMBER OF SEQ ID NOS: 5

<210> SEQ ID NO 1
<211> LENGTH: 16
<212> TYPE: PRT
<213> ORGANISM: Artificial Sequence
<220> FEATURE:
<223> OTHER INFORMATION: Synthetic

<400> SEQUENCE: 1

Arg Ala Asp Cys Arg Ala Asp Cys Arg Ala Asp Cys Ala Ala Ala Cys
1               5                   10                  15

<210> SEQ ID NO 2
<211> LENGTH: 4
<212> TYPE: PRT
<213> ORGANISM: Artificial Sequence
<220> FEATURE:
<223> OTHER INFORMATION: Synthetic
<223> OTHER INFORMATION: any amino acid
<220> FEATURE:
<221> NAME/KEY: REPEAT
<222> LOCATION: (1)...(4)
<223> OTHER INFORMATION: 2 - 8 sequence repetitions

<400> SEQUENCE: 2

Arg Ala Asp Xaa
```

```
1

<210> SEQ ID NO 3
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: REPEAT
<222> LOCATION: (1)...(4)
<223> OTHER INFORMATION: 2 - 8 sequence repetitions

<400> SEQUENCE: 3

Arg Ala Asp Ser
 1

<210> SEQ ID NO 4
<211> LENGTH: 4
<212> TYPE: PRT
<213> ORGANISM: Artificial Sequence
<220> FEATURE:
<223> OTHER INFORMATION: Synthetic
<223> OTHER INFORMATION: any amino acid
<220> FEATURE:
<221> NAME/KEY: REPEAT
<222> LOCATION: (1)...(4)
<223> OTHER INFORMATION: 2 - 8 sequence repetitions

<400> SEQUENCE: 4

Glu Ala Lys Xaa
 1

<210> SEQ ID NO 5
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: REPEAT
<222> LOCATION: (1)...(4)
<223> OTHER INFORMATION: 2 - 8 sequence repetitions

<400> SEQUENCE: 5

Glu Ala Lys Ser
```